United States Patent
Janas et al.

(10) Patent No.: US 10,737,262 B2
(45) Date of Patent: Aug. 11, 2020

(54) DEVICE AND METHOD FOR SEPARATING CELLS

(71) Applicant: GE Healthcare UK Limited, Buckinghamshire (GB)

(72) Inventors: Michelle Louise Janas, Cardiff (GB); Michael John Smith, Cardiff (GB)

(73) Assignee: GE Healthcare US Limited, Buckinghamshire (GB)

( * ) Notice: Subject to any disclaimer, the term of this patent is extended or adjusted under 35 U.S.C. 154(b) by 190 days.

(21) Appl. No.: 15/514,381

(22) PCT Filed: Oct. 15, 2015

(86) PCT No.: PCT/EP2015/073848
§ 371 (c)(1),
(2) Date: Mar. 24, 2017

(87) PCT Pub. No.: WO2016/059141
PCT Pub. Date: Apr. 21, 2016

(65) Prior Publication Data
US 2017/0297016 A1    Oct. 19, 2017

(30) Foreign Application Priority Data
Oct. 16, 2014   (GB) .................................... 1418382.6

(51) Int. Cl.
*B01L 3/00*     (2006.01)
*G01N 33/49*    (2006.01)

(52) U.S. Cl.
CPC ........ *B01L 3/50215* (2013.01); *G01N 33/491* (2013.01); *B01L 2200/087* (2013.01);
(Continued)

(58) Field of Classification Search
CPC ......... B01L 3/50215; B01L 2300/0803; G01N 15/05; G01N 33/491; G01N 15/042
See application file for complete search history.

(56) References Cited

U.S. PATENT DOCUMENTS 3,741,400 A * 6/1973 Dick ..................... B01L 3/5021
                                                        210/516
4,290,300 A    9/1981 Carver
(Continued)

FOREIGN PATENT DOCUMENTS

EP    1014088 A2    6/2000
FR    2350274 A1    12/1977
(Continued)

OTHER PUBLICATIONS

International Search Report and Written Opinion regarding International Application No. PCT/EP2015/073848, dated Jan. 18, 2016, 12 pages.
(Continued)

*Primary Examiner* — Jill A Warden
*Assistant Examiner* — Dwayne K Handy
(74) *Attorney, Agent, or Firm* — Eversheds Sutherland (US) LLP

(57) ABSTRACT

The invention relates to devices, methods and kits for separating biological materials, particularly populations of cells of different densities. The invention finds particular utility in the separation of blood into its different component parts or cellular populations. An insert for a centrifuge tube is disclosed that facilitates the effective separation of blood fractions by achieving a sharp and distinct interface between the density gradient medium and the blood sample. Methods and kits involving the use of the insert in separating cells are described.

21 Claims, 8 Drawing Sheets

(52) U.S. Cl.
CPC ............ *B01L 2300/0803* (2013.01); *B01L 2300/0832* (2013.01); *B01L 2300/0858* (2013.01)

(56) References Cited

U.S. PATENT DOCUMENTS

| | | | |
|---|---|---|---|
| 5,030,341 A * | 7/1991 | McEwen | B01L 3/50215 |
| | | | 210/515 |
| 5,314,074 A | 5/1994 | Inbar et al. | |
| 5,707,876 A | 1/1998 | Levine | |
| 2002/0061807 A1 | 5/2002 | Anderson | |
| 2002/0081569 A1 | 6/2002 | Anderson | |
| 2014/0087360 A1 * | 3/2014 | Woodside | G01N 33/491 |
| | | | 435/2 |

FOREIGN PATENT DOCUMENTS

| | | |
|---|---|---|
| JP | S50157574 U | 12/1975 |
| WO | 2011/126866 A1 | 10/2011 |
| WO | 2012/149641 A1 | 11/2012 |

OTHER PUBLICATIONS

Chinese Office Action for CN Application No. 201580055640.5 dated Nov. 12, 2018 (19 pages with English translation).
Japanese Office Action for JP Application No. 2017-518452 dated May 21, 2019 (5 pages with English translation).

* cited by examiner

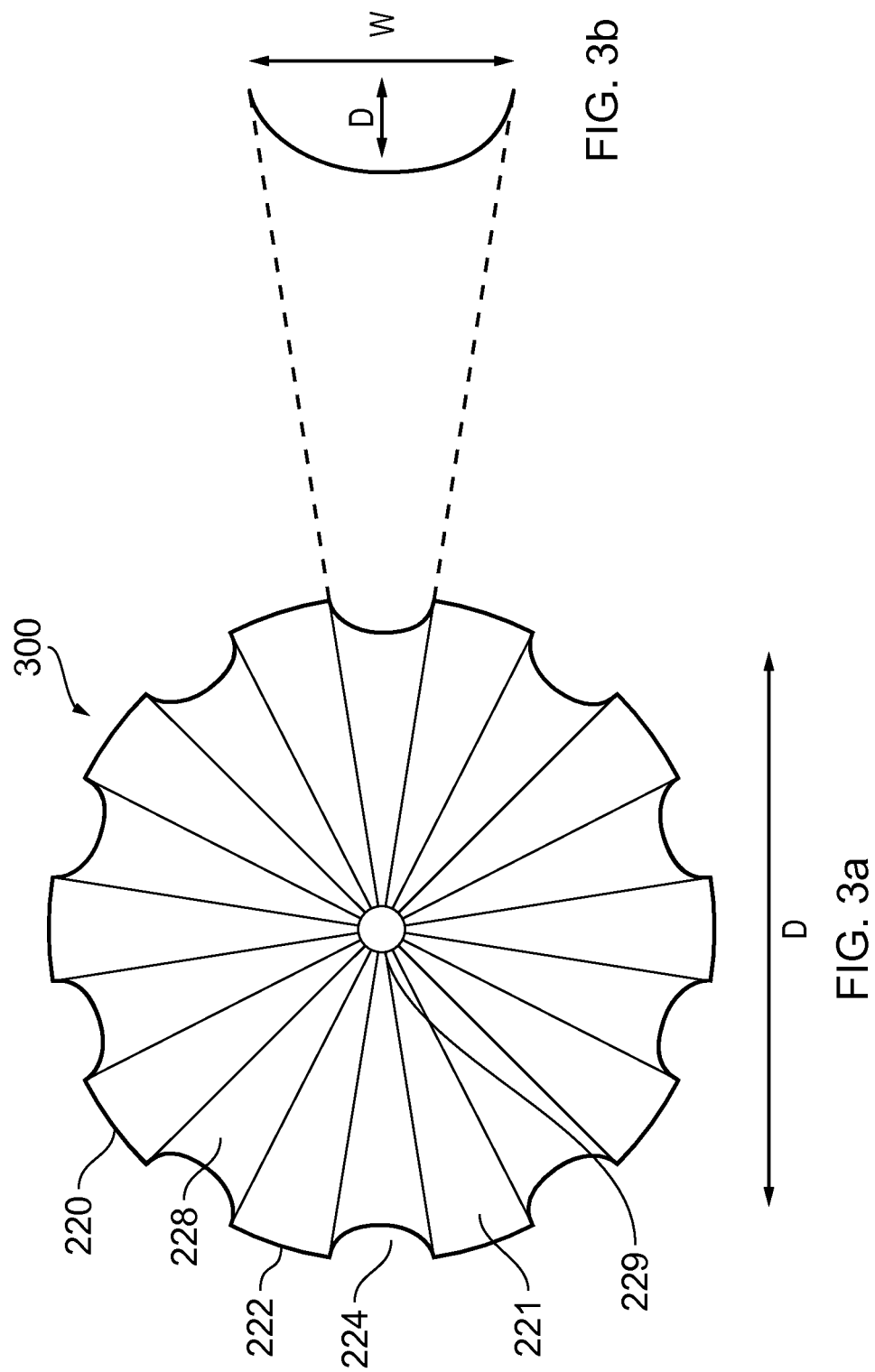

DEVICE AND METHOD FOR SEPARATING CELLS

CROSS-REFERENCE TO RELATED APPLICATIONS

This application is a filing under 35 U.S.C. 371 of international application number PCT/EP2015/073848, filed Oct. 15, 2015, which claims priority to GB application number 1418382.6, filed Oct. 16, 2014, the entire disclosures of each of which are hereby incorporated by reference.

TECHNICAL FIELD OF THE INVENTION

The invention relates to devices, methods and kits for separating biological materials, particularly populations of cells of different densities. The invention finds particular utility in the separation of blood into its different component parts or cellular populations.

BACKGROUND TO THE INVENTION

In medicine and biology, density gradients are commonly used to separate blood into distinct fractions such as red blood cells, white blood cells and plasma. The blood is overlayered onto a medium of defined density (e.g. Ficoll™, Ficoll-Paque™, GE Healthcare) and then centrifuged. During the centrifugation process, differential migration of the blood components occurs, resulting in the formation of layers of each blood fraction. Red blood cells migrate through the Ficoll layer and sediment at the bottom of the tube while white blood cells move to the interface above the Ficoll and below the plasma layers. White blood cells nominally comprise less than 1% of peripheral blood and this technique allows for their effective and facile purification.

For the effective separation of blood fractions the interface between the density gradient medium and the blood sample must be as sharp as possible, with minimal mixing. This can be difficult to achieve and a skilled, steady hand and patience are required. As such the loading of blood onto a density gradient medium prior to centrifugation is very time consuming. The interface is also fragile and if the tube is knocked the interface can easily mix and be destroyed. The removal or harvesting of the separated bands or fractions following centrifugation also poses technical challenges for the operator who must take care not to disrupt or destroy the fractions and to avoid excessive carry-over of density gradient medium.

Methods and devices have been developed to address these problems.

WO2012/149641 (Stem Cell Technologies Inc.) describes an insert for a centrifuge tube which aids density gradient separation of different cellular populations present in a sample. The insert is sized to fit into a centrifuge tube, and has a member which is positioned or stabilized within the tube by a support, typically a cylindrical support, thereby dividing the tube into a top and bottom portion. The member is typically of a concave configuration and has at least two openings, one of which is closer to the bottom end of the tube when the insert is in position and acts to allow liquid to pass through it to the bottom portion, the second acting to allow air to escape to equalize pressure. Centrifuge tubes incorporating such inserts are commercially available, i.e. SepMate™ from Stem Cell Technologies Inc.

Accuspin™ tubes, available from Sigma-Aldrich, are designed for use with density gradient medium, such as Histopaque®, for the isolation of lymphocytes and other mononuclear cells. The Accuspin tube (also known as a Leucosep™ tube available from Greiner Bio-One) is a specially designed polypropylene centrifugation tube with two chambers separated by a porous high density polyethylene barrier or frit. The density gradient medium, such as Histopaque-1077, is added to the lower chamber below the frit. The blood sample is added to the top chamber and the tube centrifuged. On centrifugation, the red blood cells sediment to the bottom of the tube containing the density gradient medium, while mononuclear cells such as lymphocytes and monocytes form a dense band at the plasma/Histopaque-1077 interface. This band can then be removed by decanting or with a pipette. Contamination with red blood cells is avoided due to the barrier between the chambers.

Floaties™ (www.Biofloaties.com) are small autoclavable polymer blend beads which are designed for the in vitro isolation of peripheral blood mononuclear cells (PBMC's) from human whole blood and cord blood samples by density gradient centrifugation. The beads are poured directly onto the top of the density gradient medium in a centrifuge tube and the blood sample gently added. The majority of the beads rise to the top of the sample which may then be centrifuged in the tube. Following centrifugation, the PBMC's form a layer or band near the plasma-density gradient medium interface, and are collected by inserting a pipette through the layer of beads.

Although a number of commercial products are available for overcoming the aforementioned problems, there is still a need for a simple and flexible means for achieving an effective separation of blood fractions in a cost effective manner. The present invention addresses this need by the provision of novel inserts, methods, centrifuge tubes and kits.

SUMMARY OF THE INVENTION

According to a first aspect of the present invention, there is provided an insert (100) for a centrifuge tube comprising a disc (20) sized to fit into a centrifuge tube for dividing said tube into an upper portion and a lower portion; said disc (20) comprising a convex upper surface (21) and an outer edge (22) having one or more indentations (24) therein; and a prop (30) extending from a lower surface (26) of the disc (20) for contacting the base of said tube when the insert (100) is positioned within the tube.

In one embodiment, the one or more indentations (24) allow fluid communication between the upper portion and the lower portion of the tube.

In another embodiment, the one or more indentations (24) are sized to create a surface tension across the one or more indentations (24) to restrict the flow of liquid therethrough in the absence of a centrifugal force.

In a further embodiment, the upper surface (21) additionally comprises one or more grooves (28) connected to said one or more indentations (24).

In one embodiment, the upper surface (21) of the disc (20) additionally comprises a gripping element (40).

In another embodiment, the gripping element (40) is in the centre of the upper surface (21) of the disc (20). Preferably, the gripping element (40) is in the form of a rod.

In a further embodiment, the one or more groves (26) connect the centre of the disc (20) with the one or more indentations (24).

In one embodiment, the grooves (26) are fan shaped, being narrower at the centre of the disc (20) than at the indentations (24).

In another embodiment, lower surface (28) of the disc (20) is convex in form.

In a further embodiment, the one or more indentations (24) are semi-circular or oval in form.

In one embodiment, the insert is composed of a polymer. Preferably the polymer is an inert polymer. Preferably the polymer is sterilisable, for example by autoclaving, chemical treatment or by irradiation with suitable energy such as γ rays. Typically the polymer is a plastic polymer such as polyethylene or polypropylene. However, other inert plastic polymers may be used such as polycarbonate, polyvinyl and acrylate polymers.

In another embodiment, the insert has been treated to minimize microbial contamination. Examples of suitable methods include autoclaving, chemical treatment with disinfectants or antimicrobial agents, and/or irradiation with suitable energy such as γ rays.

In accordance with a second aspect of the present invention, there is provided a centrifuge tube comprising an insert as hereinbefore described. The centrifuge tube may additionally contain a density gradient medium.

According to a third aspect of the present invention, there is provided a method for separating cells comprising the steps of.
 i) adding a volume of density gradient medium to a centrifuge tube;
 ii) positioning an insert as hereinbefore described on the surface of said density gradient medium such that the prop is in contact with the base of said tube;
 iii) dispensing a liquid sample containing one or more cells over the upper surface of the disc to form an interface between the density gradient medium and the sample; and
 iv) centrifuging the tube to separate said one or more cells from the sample.

In one embodiment, the cells are selected from the group consisting of mammalian cells, red blood cells, white blood cells and stem cells.

In another embodiment, the sample comprises whole blood.

In a further embodiment, the method additionally comprises the step of recovering the one or more cells.

In accordance with a fourth aspect of the present invention, there is provided a kit comprising an insert as hereinbefore described and a centrifuge tube. Preferably, the kit additionally comprises a volume of density gradient medium.

According to a fifth aspect of the present invention, there is provided an insert as hereinbefore described and a volume of density gradient medium.

In accordance with a sixth aspect of the present invention, there is provided the use of an insert as hereinbefore described for separating one or more cells from a sample.

DEFINITIONS

As used herein, the term "insert for a centrifuge tube" is intended to mean any device or apparatus which may be reversibly or irreversibly placed or secured within a centrifuge tube.

Centrifuge tubes are tubes which can be centrifuged. The tubes may have conical bottom ends which are common in the art or may be flat or round-bottomed. Examples of centrifuge tubes which are commercially available include, but are not limited to, Nunc™ conical sterile polypropylene centrifuge tubes (Thermo Scientific™), Nalgene™ Oak Ridge polycarbonate, polypropylene or Teflon™ tubes (Thermo Scientific™), and Sterilin polypropylene tubes (Camlab, UK).

It will be understood that the insert according to the invention can be used with centrifuge tubes of varying volumes, such as for example, 2 ml, 5 ml, 10 ml, 15 ml and 50 ml.

In one aspect, the "cell" used in the present invention is a mammalian cell, preferably a human cell. Examples of mammalian cells that may be used in the present invention include but are not limited to blood cells, such as red blood cells (erythrocytes), white blood cells (including leukocytes, lymphocytes, granulocytes and monocytes), platelets (thrombocytes) and stem cells (e.g. hematopoietic stem cells).

The "cell" may be a bone marrow cell.

The term "stem cells" as used herein concerns pluripotent or multipotent stem cells. Examples of stem cells include, but are not limited to, embryonic stem cells (ESC), adult stem cells, haematopoietic stem cells, neural stem cells, mesenchymal stem cells and induced pluripotent stem cells (iPS).

BRIEF DESCRIPTION OF THE DRAWINGS

FIG. 3a is a schematic diagram showing a plan perspective of an insert according to the invention with detailed inset of a groove (FIG. 3b).

DETAILED DESCRIPTION OF THE DRAWINGS

Figure 1:
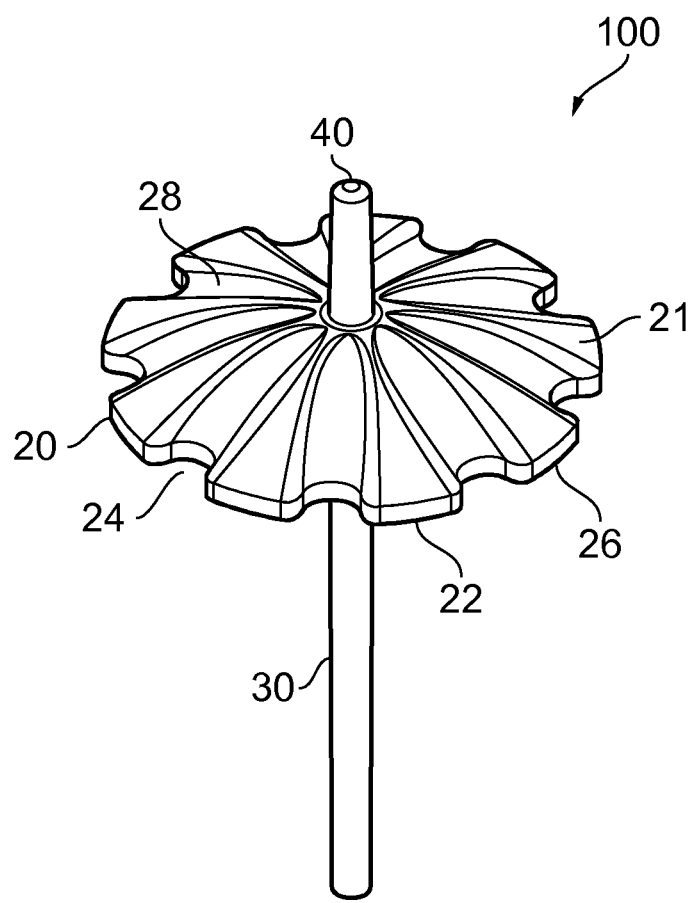
FIG. 1 shows a three dimensional perspective view of an embodiment of an insert according to the invention.

An embodiment of an insert according to the invention is shown in three dimensional perspective in FIG. 1. The insert (100) consists of a disc (20) which has a diameter which is dimensioned or sized to fit into a centrifuge tube (not shown) such that once it is in position within the tube it will divide the tube into an upper and lower portion. The insert can be sized to fit into any centrifuge tube, including those of standard volumes such as 10, 15 or 50 ml which are fabricated from suitable materials such as plastic, metal or glass. The insert acts to minimize the mixing of liquids of different densities which occurs when a liquid containing a target (such as blood cells) to be separated into another liquid is added to a first liquid of different density as this leads to poor separation of the target into the first liquid on centrifugation. The insert also facilitates the separation of the target into the first liquid during the centrifugation process. Typically the first liquid is a density gradient medium and the liquid containing the target is an aqueous blood sample.

The disc (20) has an upper surface (21) which is convex in form and has a plurality of indentations (24) in its outer edge (22) or circumference; the indentations can take any form but are generally curved, semi-circular or oval in shape. A prop (30) extending from the lower surface (not shown) of the disc (20) acts as a leg to support the disc (20) above the base of a centrifuge tube (not shown) when the insert (100) is positioned within the tube. The length of prop (30) is sized dependent on the volume of liquid to be added to the centrifuge tube, such that when the insert is added to this volume of liquid the underside of the disc will be in contact with the meniscus of the liquid. A gripping element (40) facilitates positioning and removal of the insert (100) within the centrifuge tube. The insert may be positioned and/or removed from a centrifuge tube manually, for example by use of an operator's fingers or a suitable tool such as a pair of forceps, or by automated or robotic means.

Grooves (28) connect the centre of the disc (20) with the indentations (24). The purpose of the grooves (28) is to channel liquid, which may be poured onto the convex upper surface (21) of the disc (20), to the indentations (24) so that the liquid is layered on top of a first liquid, such as density gradient medium, which is present in the lower portion of the tube with minimal disruption or mixing as this will impair the separation process.

Figure 2A:
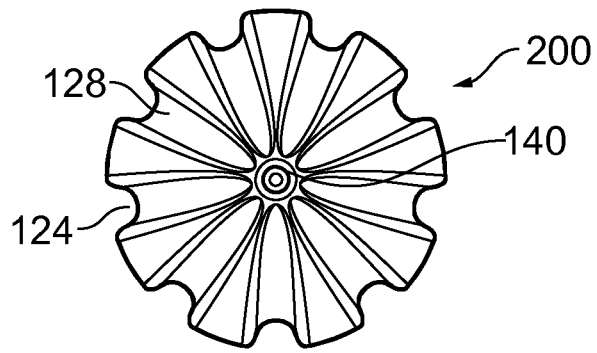
FIGS. 2a to c depict a series of views of the insert of FIG. 1: a plan perspective (FIG. 2a), a front perspective (FIG. 2b), and an underside plan perspective (FIG. 2c).
Figure 2B:
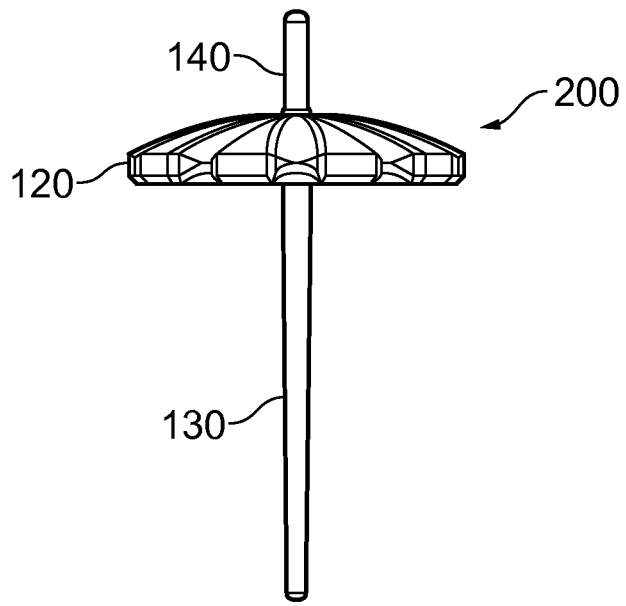
Figure 2C:
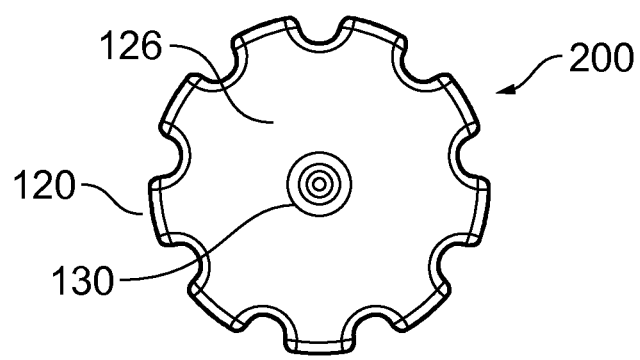

FIGS. 2a, 2b and 2c are top plan, front perspective and bottom plan views, respectively, of the insert (200) of FIG. 1. FIG. 2a provides a top plan view of the insert (200), showing the arrangement of grooves or channels (128) running from the gripping element (140) in the centre of the disc (120) to the indentations (124) on the outer edge (122) or rim of the disc (120). The gripping element (140) and prop (130) of the insert (200) are shown in the front perspective view of FIG. 2b. The underside plan view FIG. 2c of the insert (200) shows the concave lower surface (126) of the disc (120) with central prop (130).

A schematic top plan view of a disc (220) of an embodiment of an insert (300) according to the invention is illustrated in FIG. 3a. In the example, the disc (220) has fan shaped grooves extending radially from its centre (229) of its upper surface (221) to indentations (224) in the outer edge (222), the grooves (228) being narrower at the centre of the disc than at the outer edge. The diameter (D) of the disc (220) will vary depending on the size or volume of the centrifuge tube for which the insert is intended; for example, a typical insert for a 50 ml centrifuge tube would have a disc of approximate diameter 26 mm. For such an insert, the curved indentations would be approximately 4 mm in width (W) and have a depth (D) of approximately 1 mm (FIG. 3b).

Figure 4B:
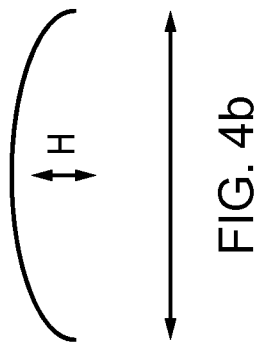
FIGS. 4a, b and c are schematic diagrams of a portion of an inset according to the invention. In particular, FIG. 4a details the flow of a liquid over the upper surface of the disc of the insert, FIG. 4b the height of the rise and FIG. 4c the depth of the groove.
Figure 4C:
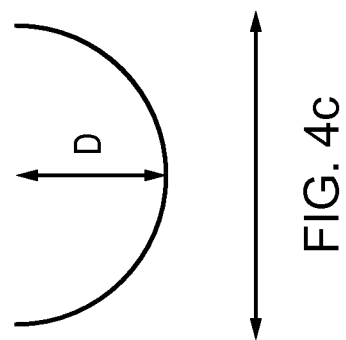
Figure 4A:
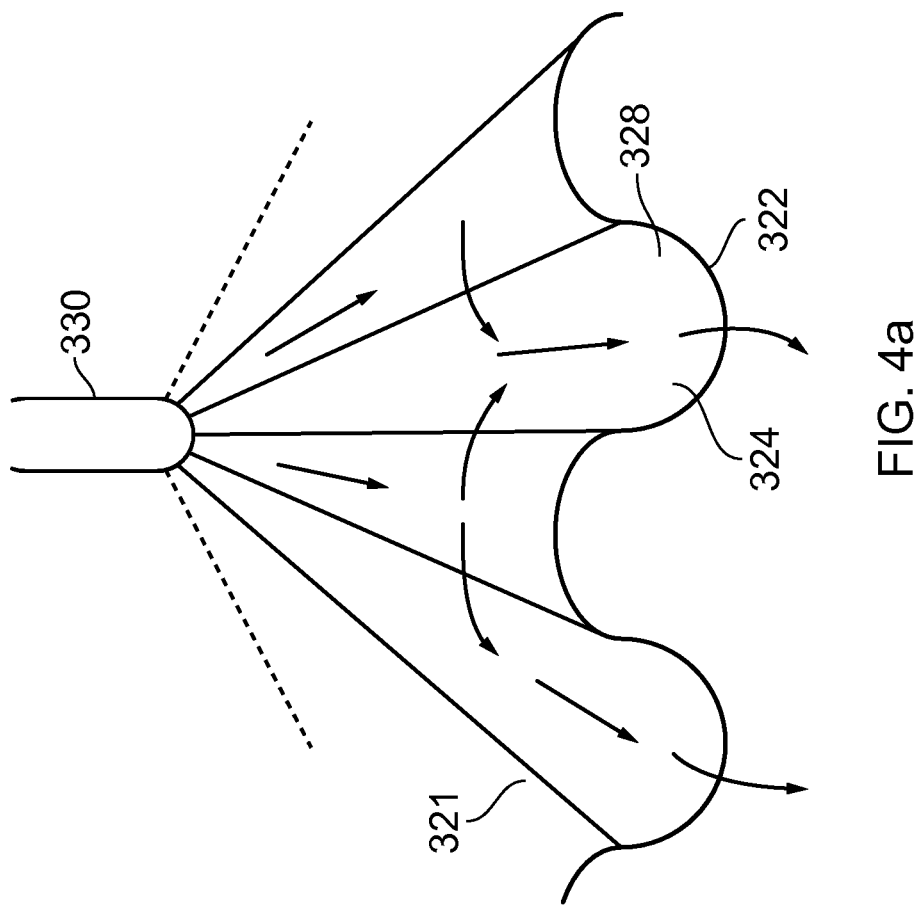

FIGS. 4a, b and c show schematic views of a portion of a disc of an embodiment of the invention. FIG. 4a depicts the flow of a liquid (as illustrated by the direction of flow of the arrows) over the upper surface (321) of the disc. Liquid poured onto the top of the convex upper surface of the disc runs into the fan shaped grooves (328), flows down their length into the indentations (324) and then from the surface of the disc. The depth of the grooves (328) increases from the centre of the disc where it meets with the gripping element (330) to a maximum at its outer edge (322). FIG. 4b is a schematic detail showing the height of the rise (H) of the non-inundated rim on the outer edge (322) of the disc, which for an insert for a 50 ml centrifuge tube would be approximately 1 mm. FIG. 4c shows the depth (D) of the groove (328), which would be approximately 1 mm for the insert shown. The depth D and height H would vary depending upon the volume of the tube for which the insert was designed.

Figure 5C:
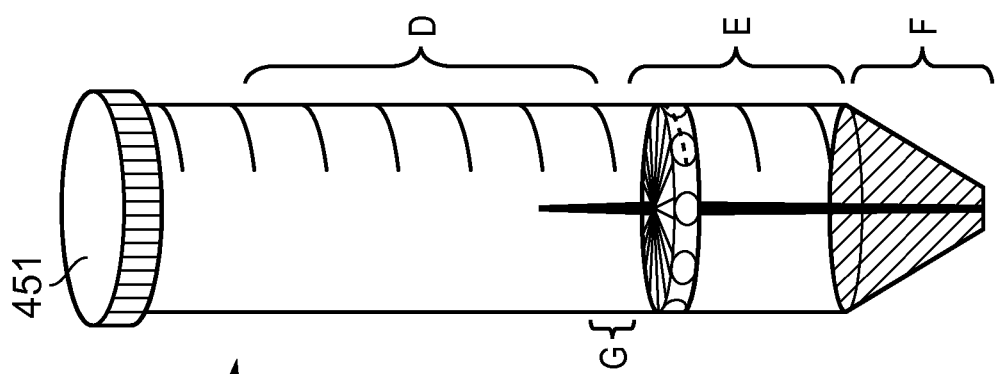
FIGS. 5a), b) and c) are schematic representations of an insert according with the invention positioned within an empty centrifuge tube (FIG. 5a) and a filled centrifuge tube (FIG. 5b) prior to centrifugation, and following centrifugation (FIG. 5c).
Figure 5B:
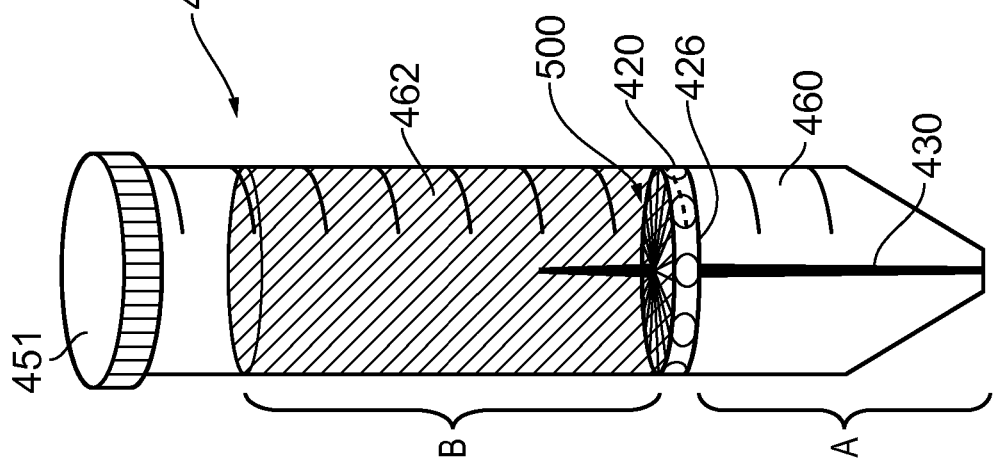
Figure 5A:
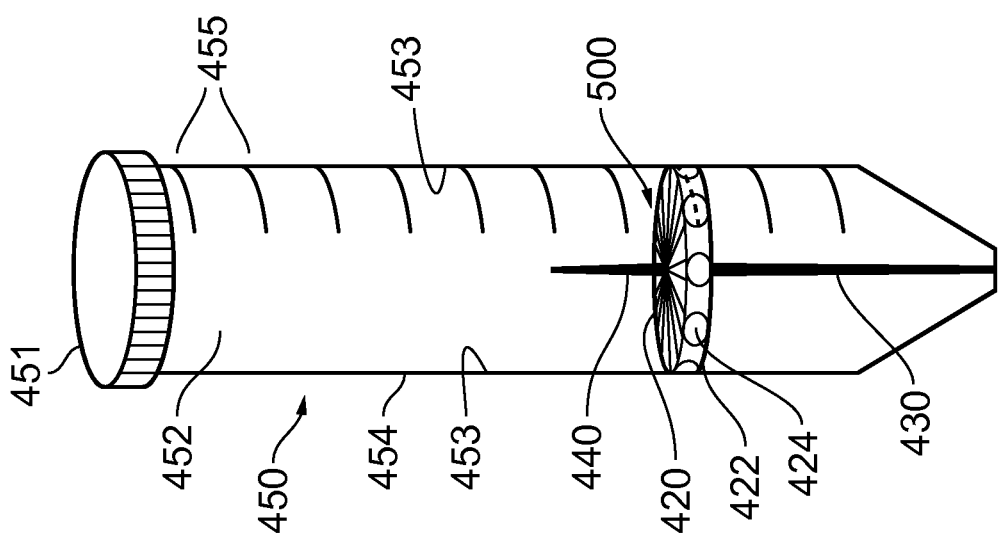

FIGS. 5a, b and c are schematic representations of an insert in accordance with the invention positioned within an empty centrifuge tube (FIG. 5a), a filled centrifuge tube prior to (FIG. 5b) and following centrifugation (FIG. 5c).

FIG. 5a shows an insert (500) according to the invention positioned within a conventional centrifuge tube (450), the tube having a lid (451) enclosing a hollowed interior (452) or chamber defined by its interior walls (453). The centrifuge tube (450) of FIG. 5a does not contain any liquid. Both the exterior (453) and interior (454) walls of the tube are made from an inert material, such as plastic, glass or metal. The centrifuge tube (450) may be designed to accommodate a range of liquid volumes, such as 5 ml, 10 ml, 15, and 50 ml, the walls being marked (455) to indicate the volume present within the chamber (452).

The insert (500) comprises a disc (420), with gripping element (440) to allow positioning within the tube (450) and prop (430) to support the disc above the base of the tube. The disc is sized such that the outer edge (422) is in contact with the interior walls (453) of the tube (450) to present a liquid impermeable barrier, such that liquid cannot pass from the upper portion of the tube to the lower portion of the tube except through indentations (424). The indentations (424), present in the outer edge of the disc, are designed to restrict flow of liquid across the disc in the absence of centrifugal force.

FIG. 5b illustrates the tube (450) of FIG. 5a filled with two liquids (460 and 462), a density gradient medium (460) and a liquid sample (462) containing cells, prior to centrifugation and separation of the cells from the liquid sample (462) into the density gradient medium. To prepare the tube shown in FIG. 5b, a pre-defined volume of density gradient medium (460) is poured into the lower portion (A) of the tube and insert (500) subsequently inserted such that the meniscus of liquid (460) is in fluid connection with the lower surface (426) of disc (420) of the insert when it is supported above the base of the tube by prop (430). The length of the prop (430) thus acts as a spacer to define a specific volume of liquid (460) or density gradient medium which can be present in the lower portion (A) of the centrifuge tube. It will be understood that the length of the prop (430) will vary depending upon the desired volume of liquid or density gradient medium (460) to be used in the centrifugation and separation process, and the internal volume of the centrifugation tube. For a typical 50 ml centrifuge tube, the length of the prop (430) is sized such that the disc (420) sits at the 15 ml mark of the tube (450).

A liquid sample (462) containing cells, such as blood cells, is carefully poured onto the upper surface of the disc (420) to form a layer above it in the upper portion (B) of the tube. The cap (451) is then replaced and the tube is transferred to a centrifuge.

FIG. 5c is a schematic representation of the tube of FIG. 5b following centrifugation. The liquid present in the tube (450) has separated into four fractions, D, E, F and G based upon density. Fraction D primarily contains plasma, fraction E is Ficoll, fraction F consists predominantly of red blood cells, and fraction G contains white blood cells. The target populations of cells can now be collected by carefully pipetting the various fractions from the tube: for example, if white blood cells are required then fraction D is first removed and then fraction G collected. Alternatively, if red blood cells are targeted, fractions D and G are discarded, the insert (500) carefully removed to avoid disturbing and remaining fractions, and fraction F collected.

EXPERIMENTAL

The invention will now be described with reference to the specific examples below.

An insert according to the invention was tested for its ability to assist with the loading of blood onto a Ficoll-Paque density gradient medium without mixing at the Blood-Ficoll interface and for its ability to allow blood fractions to separate without mixing under centrifugal force.

25 ml of blood was diluted two fold with phosphate buffered saline (PBS) containing 2% human serum. 15 ml of Ficoll-Paque was added to 3×50 ml centrifuge tubes. Two tubes were conventional centrifuge tubes (550a and 550c of FIG. 6) while one tube (550b of FIG. 6) was an Accuspin™ tube (Sigma-Aldrich). Accuspin™ tubes are specially designed polypropylene centrifuge tubes with two chambers separated by a porous high density polytheylene barrier or frit to aid the separation of lymphocytes and other mononuclear cells from whole blood and bone marrow during centrifugation.

25 mls of the blood/PBS mix (562a, 562b) was carefully pipetted onto the surface of the Ficoll-Paque layer of both tube 550a and b. An insert (600) according to the invention was added to the third tube (550c). 25 ml of the blood/PBS mix (562c) was added by pipetting to the top centre of the insert in tube 550c to allow the blood mix to flow down the grooves and form a layer above the Ficoll-Paque layer.

Figure 6:
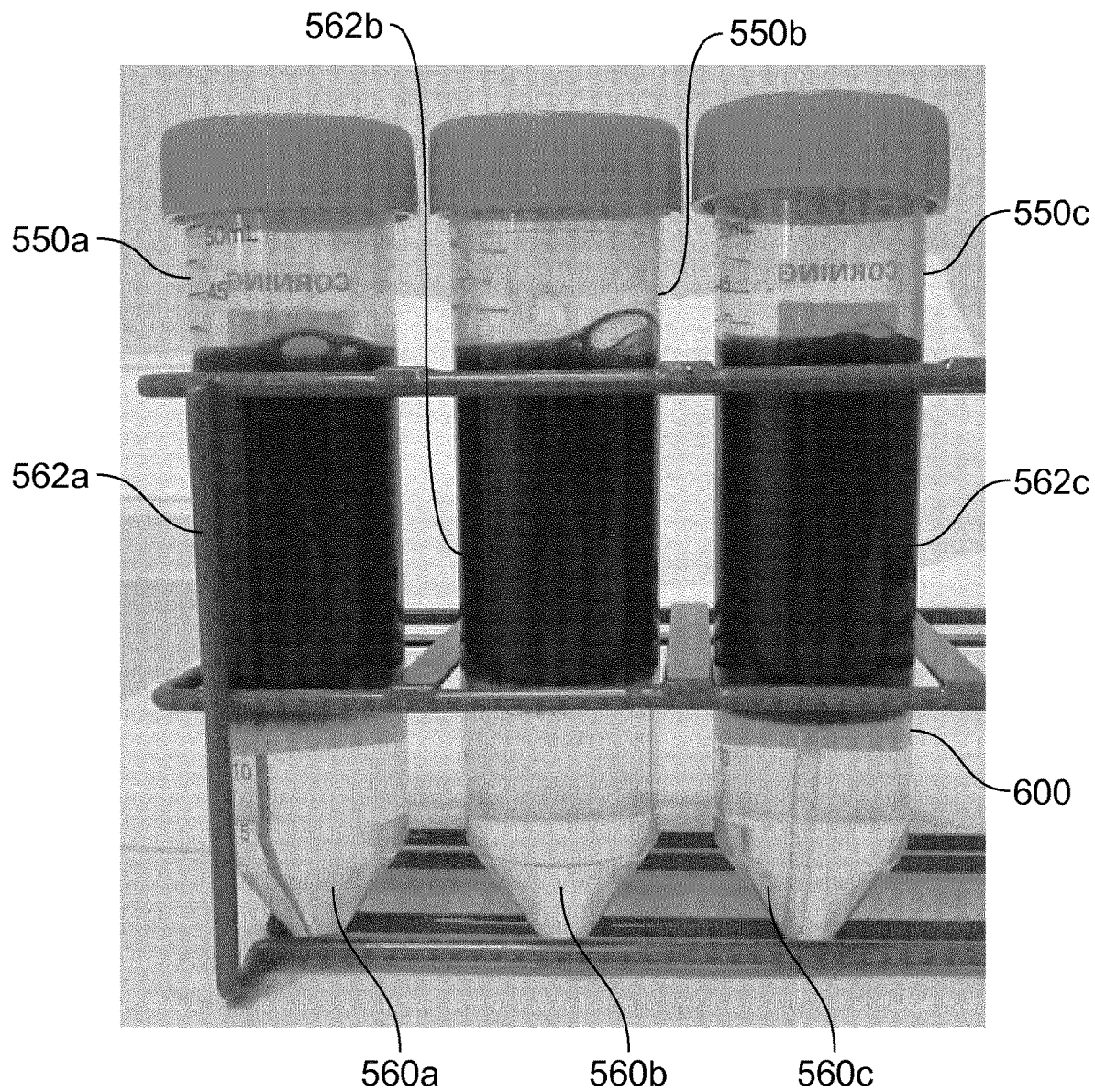
FIG. 6 is a photograph of three centrifuge tubes (550a, 550b and 550c) which have been loaded with a Ficoll-Paque density gradient medium (lower layer, 560a, b and c) and a blood/PBS mix (upper layer, 562a, b and c) prior to separation by centrifugation.

FIG. 6 is a photograph of the three tubes (550a, 550b and 550c) which have been loaded with a Ficoll-Paque density gradient medium (lower layer, 560a, b and c) and the blood/PBS mix (upper layer, 562a, b and c) prior to separation by centrifugation. As can be seen, two of the tubes 550a and 550c are conventional centrifuge tubes (tube 550c containing an insert 600 according to the invention) while tube 550b is an Accuspin™ tube (Sigma-Aldrich).

All three tubes were centrifuged at 400 g for 30 minutes with the brake off.

Figure 7:
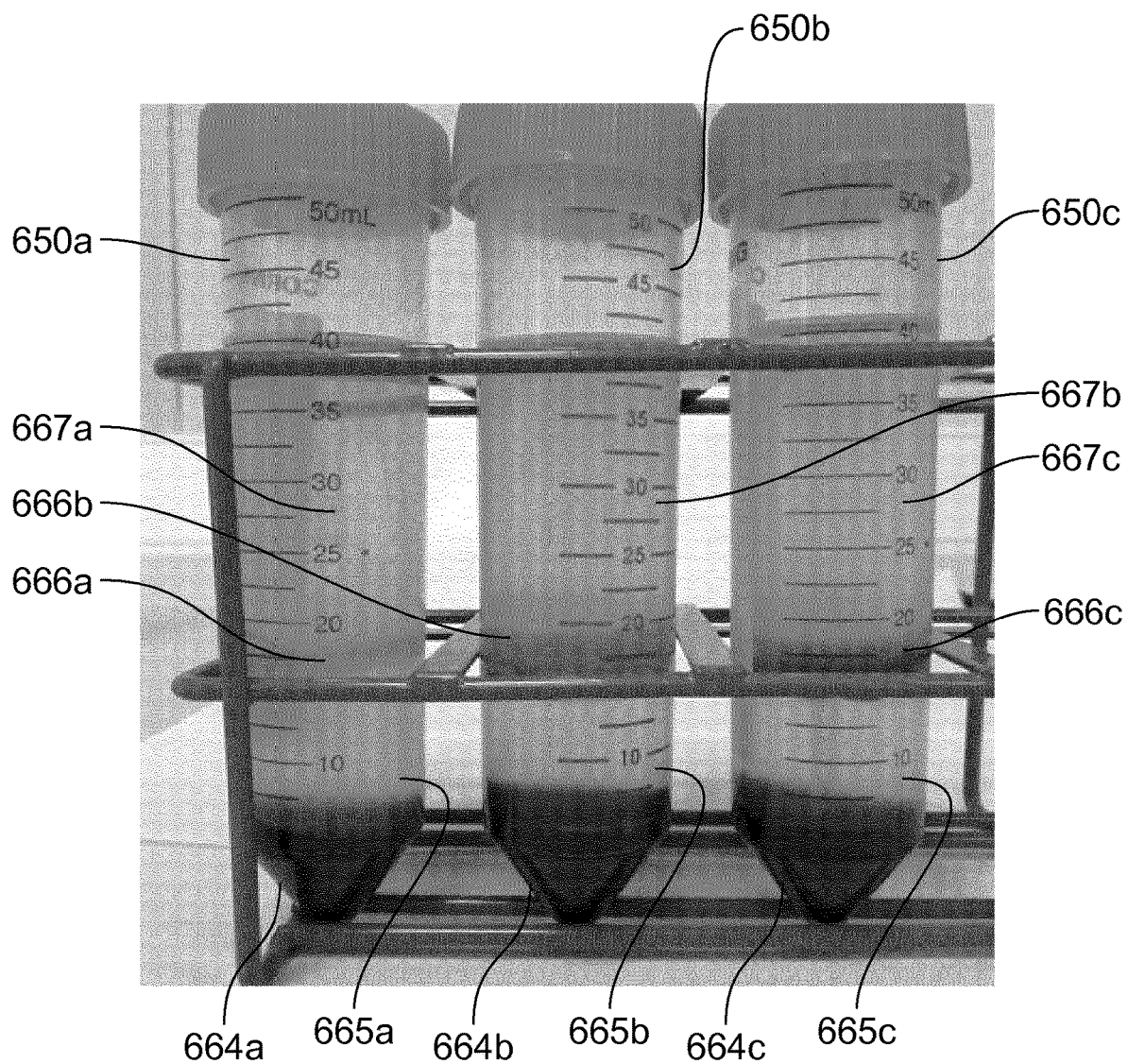
FIG. 7 is a photograph of the three centrifuge tubes shown in FIG. 6 following centrifugation and the separation process.

FIG. 7 shows the same three tubes of FIG. 6 following centrifugation and the separation process. The red blood cells have pelleted at the bottom (664a, b and c) of the Ficoll-Paque layer (665a, b and c) of the tubes (650a, b and c) while the white blood cells (666a, b and c) have separated at the interface of the Ficoll-Paque (665a, b and c) and the plasma 667 (a, b and c) layers.

The white blood cell fractions from each tube were then harvested with a pipette and counted using a nucleocounter (NC100, Sartorius). $10^6$ cells were analysed by flow cytometry (FACS Calibur, BD Bioscience) to determine their population composition.

Figure 8:
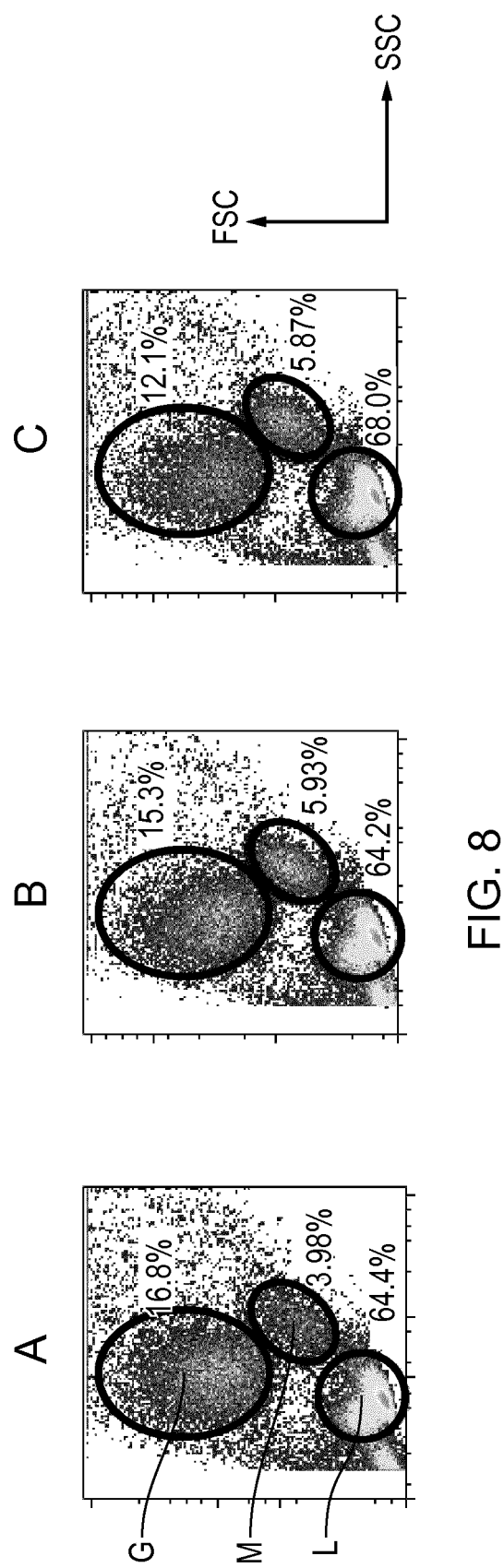
FIG. 8 is a graphical representation of the results from the flow cytometry analysis of the white blood cell fraction from each of the tubes (A corresponds to 650a, B to 650b and C to 650c) of FIG. 7, the letters G indicating the Granulocyte sub-population, M the Monocyte sub-population and L the Lymphocyte sub-population present in the white blood cell fractions. FSC and SSC signify forward scatter and side scatter, respectively.

FIG. 8 is a graphical representation of the results from the flow cytometry analysis of the white blood cell fraction from each of the tubes (A corresponds to 650a, B to 650b and C to 650c) of FIG. 7, the letters G indicating the Granulocyte sub-population, M the Monocyte sub-population and L the Lymphocyte sub-population present in the white blood cell fractions. The figures also show the percentage of each sub-population (Granulocytes, Monocytes and Lymphocytes) present in the white blood-cell population. Table 1 below gives the white blood cell recovery and cell viability for each of the tubes.

|  | White Blood Cell Recovery | Cell Viability |
| --- | --- | --- |
| Tube containing No Insert (e.g. Tube 650a) | $2.24 \times 10^8$ | 98.9% |
| Accuspin™ Tube (Tube 650b) | $2.91 \times 10^8$ | 99.1% |
| Insert containing Tube (Tube 650c) | $2.12 \times 10^8$ | 99.1% |

N = 1

As can be seen, there is no discernible difference in the white blood cells that have been harvested using conventional Ficoll-Paque layering or using the Accuspin™ tube, compared to using the insert according to the invention, in terms of total cell count, cell viability or population of the cells.

While preferred illustrative embodiments of the present invention are described, one skilled in the art will appreciate that the present invention can be practiced by other than the described embodiments, which are presented for purposes of illustration only and not by way of limitation. The present invention is limited only by the claims that follow.

The invention claimed is:

1. An insert for a centrifuge tube, the insert comprising:
a disc sized to fit into a centrifuge tube and configured for dividing the centrifuge tube into an upper portion and a lower portion;
the disc comprising an upper surface having a convex shape, an outer edge having one or more indentations defined therein, wherein the one or more indentations are configured for allowing fluid communication between the upper portion and the lower portion of the centrifuge tube, and one or more grooves defined in the upper surface and connected to the one or more indentations, wherein the one or more grooves extend in a radial direction with respect to a center of the disc; and
a prop extending from a lower surface of the disc and configured for contacting a base of the tube when the insert is positioned within the centrifuge tube.

2. The insert according to claim 1, wherein the one or more indentations are sized to create a surface tension across the one or more indentations to restrict the flow of liquid therethrough in the absence of a centrifugal force.

3. The insert according to claim 1, further comprising a gripping element extending from the upper surface of the disc.

4. The insert according to claim 3, wherein the gripping element is positioned at a center of the upper surface of the disc.

5. The insert according to claim 3, wherein the gripping element is in the form of a rod.

6. The insert according to claim 1, wherein the one or more grooves connect a center of the disc with the one or more indentations.

7. The insert according to claim 6, wherein the one or more grooves are fan shaped, such that a width of the one or more grooves is narrower at the center of the disc than at the one or more indentations.

8. The insert according to claim 1, wherein the lower surface of the disc has a convex shape.

9. The insert according to claim 1, wherein the one or more indentations have a semi-circular or oval shape.

10. The insert according to claim 1, wherein the insert is composed of a polymer.

11. The insert according to claim 1, wherein the insert has been treated to minimize microbial contamination.

12. A centrifuge tube assembly comprising a centrifuge tube and the insert according to claim 1 positioned within the centrifuge tube.

13. The centrifuge tube assembly of claim 12, further comprising a volume of density gradient medium positioned within the centrifuge tube.

14. A method for separating cells comprising:
adding a volume of density gradient medium to a centrifuge tube;
positioning the insert according to claim 1 on a surface of the density gradient medium such that the prop is in contact with a base of the centrifuge tube;
dispensing a liquid sample containing one or more cells over the upper surface of the disc to form an interface between the density gradient medium and the liquid sample; and
centrifuging the centrifuge tube to separate the one or more cells from the liquid sample.

15. The method according to claim 14, wherein the one or more cells are selected from the group consisting of mammalian cells, red blood cells, white blood cells, and stem cells.

16. The method according to claim 14, wherein the liquid sample comprises whole blood.

17. The method according to claim 14, further comprising recovering the one or more cells.

18. A kit comprising the insert according to claim 1 and a centrifuge tube.

19. The kit according to claim 18, further comprising a volume of density gradient medium.

20. A kit comprising the insert according to claim 1 and a volume of density gradient medium.

21. A method of using the kit according to claim 20 for separating one or more cells from a liquid sample, the method comprising:
adding the volume of density gradient medium to a centrifuge tube;
positioning the insert on a surface of the density gradient medium such that the prop is in contact with a base of the centrifuge tube;
dispensing the liquid sample over the upper surface of the disc to form an interface between the density gradient medium and the liquid sample; and
centrifuging the centrifuge tube to separate the one or more cells from the liquid sample.

* * * * *